(12) United States Patent
Kaiser et al.

(10) Patent No.: US 11,398,035 B2
(45) Date of Patent: Jul. 26, 2022

(54) PARTITIONING A MEDICAL IMAGE

(71) Applicant: Brainlab AG, Munich (DE)

(72) Inventors: Hagen Kaiser, Icking (DE); Stefan Seifert, Isen (DE)

(73) Assignee: Brainlab AG, Munich (DE)

( * ) Notice: Subject to any disclaimer, the term of this patent is extended or adjusted under 35 U.S.C. 154(b) by 358 days.

(21) Appl. No.: 16/605,163

(22) PCT Filed: Jul. 17, 2018

(86) PCT No.: PCT/EP2018/069418
§ 371 (c)(1),
(2) Date: Oct. 14, 2019

(87) PCT Pub. No.: WO2020/015822
PCT Pub. Date: Jan. 23, 2020

(65) Prior Publication Data
US 2021/0407092 A1    Dec. 30, 2021

(51) Int. Cl.
*G06T 7/11* (2017.01)
*G06T 7/30* (2017.01)
(Continued)

(52) U.S. Cl.
CPC ............ *G06T 7/11* (2017.01); *A61N 5/1049* (2013.01); *A61N 5/1065* (2013.01); *G06T 7/174* (2017.01);
(Continued)

(58) Field of Classification Search
CPC ..... G06T 7/11; G06T 7/30; G06T 7/14; G06T 2207/10048; G06T 2207/20221; G06T 2207/30201; A61N 5/1049; A61N 5/1065
See application file for complete search history.

(56) References Cited

U.S. PATENT DOCUMENTS 8,463,360 B2 * 6/2013 Yamamoto ............ A61B 90/36
                                              600/427
8,918,162 B2 * 12/2014 Prokoski ................ A61B 5/418
                                              600/475
(Continued)

FOREIGN PATENT DOCUMENTS

WO    WO2017190780 A1    11/2017

OTHER PUBLICATIONS

Kakadiaris, et al., "Multimodal face recognition: combination of geometry with physiological information" IEEE Computer Society Conference on Computer Vision and Pattern Recognition. Jul. 2005.
(Continued)

*Primary Examiner* — Gregory M Desire
(74) *Attorney, Agent, or Firm* — Middleton Reutlinger

(57) ABSTRACT

Disclosed is a computer-implemented method for partitioning a medical image which encompasses acquiring a medical image of a surface of a patient and a surface of at least one object (embodied by image data), for example, by means of a 3D scanning device. Furthermore, a thermal image of the surface of the patient and the surface of the object is acquired (embodied by thermal data), for example, by means of a thermal camera. The medical image and the thermal image are fused (based on registration data), such that the image data is associated with the thermal data (embodied by association data). By analyzing the association data with regard to a specified condition (embodied by condition data), for example a condition related to a temperature threshold, a subset of the association data which fulfills the condition and describes a part of the medical image is determined (embodied by condition compliance data). For example, the object is colder than the skin of the patient, so by applying the temperature threshold, the part of the image representing the object may be identified. Accordingly, a part of the medical image showing a surface of the patient
(Continued)

may be distinguished from a part of the medical image showing a surface of the object. Furthermore, and for example, one of those two parts may be defined to be a region of interest, and a positional shift of the region of interest (e.g. a face of the patient) may be determined by tracking the region of interest.

12 Claims, 5 Drawing Sheets

(51) Int. Cl.
  *G06T 7/174* (2017.01)
  *A61N 5/10* (2006.01)
(52) U.S. Cl.
  CPC ...... *G06T 7/30* (2017.01); *G06T 2207/10048* (2013.01); *G06T 2207/20221* (2013.01); *G06T 2207/30201* (2013.01)

(56) References Cited

U.S. PATENT DOCUMENTS

| 15,098,094 | | 12/2017 | Tallhamer et al. | |
| 9,892,513 | B2* | 2/2018 | Gurevich | G16H 50/50 |
| 2005/0054910 | A1* | 3/2005 | Tremblay | A61B 5/055 600/411 |
| 2007/0257188 | A1* | 11/2007 | Robertson | G01K 11/006 374/E11.003 |
| 2008/0162352 | A1* | 7/2008 | Gizewski | G16H 50/20 705/50 |
| 2015/0098094 | A1 | 4/2015 | Weidmann et al. | |

OTHER PUBLICATIONS

Zheng "Face detection and eyeglasses detection for thermal face recognition" SPIE-IS&T vol. 8300, Alcorn State University, 2012.
International Search Report and Written Opinion issued in Application No. PCT/EP2018/069418 dated May 2, 2019; 12 Pages.
Anonymous: "Lidar—Wikipedia, version as on Jul. 15, 2018", Jul. 15, 2018 (Jul. 15, 2018), XP55685503, Retrieved from the internet: URL:https://en.wikipedia.org/w/index.php?title=Lidar&oldid= 850387824 [retrieved on Apr. 14, 2020].
Anonymous: "Kinect—Wikipedia, version as on Jun. 7, 2018", Jul. 6, 2018 (Jul. 6, 2018), XP55685506, Retrieved from the Internet: URL:https://en.wikipedia.org/w/index.php?title=Kinect&oldid= 849133515 [retrieved on Apr. 14, 2020].
European Patent Office: Communication for Application No. 18745860.9 dated Apr. 24, 2020.

* cited by examiner

PARTITIONING A MEDICAL IMAGE

FIELD OF THE INVENTION

The present invention relates to a computer-implemented method for partitioning a medical image, a computer-implemented medical method for determining a positional shift of the region of interest, a corresponding computer program, a non-transitory program storage medium storing such a program and a computer for executing the program, a medical system comprising the aforementioned computer as well as a radiation treatment system.

TECHNICAL BACKGROUND

For stereotactic radiosurgery, in particular when treating brain tumors, it is essential that the patient is positioned relative to the radiation delivery system with very high accuracy so that radiation is delivered to the tumor, and not the surrounding healthy tissue. For this reason, the head of a patient undergoing stereotactic surgery is fixated via a fixation device, such as an open face mask, so that the patient cannot move his head during treatment.

Distinguishing between different parts of a medical image is crucial. In a medical image comprising the surface of the patient and the surface of an object, like the surface of a fixation device, the respective parts of the image may be distinguished manually. However, this is cumbersome and prone to errors.

Alternatively, the fixation device may be painted with a special paint such that the region of interest and the fixation device may be distinguished automatically by means of a structured light scanner. However, special materials need to be used for the fixation device as well as the paint.

There are other areas of medicine where an image part representing a non-living object (non-mammal object) has to be distinguished from an image part representing a living object (mammal object). For instance in image guided surgery, it is of interest to distinguish during image processing an instrument or implant (example for non-mammal object) from a part of the patient (mammal object). More details about image guided surgery are disclosed in the section entitled "Definitions".

The present invention has the object of providing an improved method for partitioning a medical image.

The present invention can be used for radiation treatment procedures e.g. in connection with a system for image-guided radiotherapy such as VERO® and ExacTrac®, both products of Brainlab AG. Furthermore, the present invention may be generally used in the field of image guided surgery.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses acquiring a medical image of a surface of a patient and a surface of at least one object (embodied by image data), for example, by means of a 3D scanning device. Furthermore, a thermal image of the surface of the patient and the surface of the object is acquired (embodied by thermal data), for example, by means of a thermal camera. The medical image and the thermal image are fused (based on registration data), such that the image data is associated with the thermal data (embodied by association data). By analyzing the association data with regard to a specified condition (embodied by condition data), for example a condition related to a temperature threshold, a subset of the association data which fulfills the condition and describes a part of the medical image is determined (embodied by condition compliance data). For example, the object is colder than the skin of the patient, so by applying the temperature threshold, the part of the image representing the object may be identified. Accordingly, a part of the medical image showing a surface of the patient may be distinguished from a part of the medical image showing a surface of the object. Furthermore, and for example, one of those two parts may be defined to be a region of interest, and a positional shift of the region of interest (e.g. a face of the patient) may be determined by tracking the region of interest.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of partitioning a medical image according to claim 1. The method comprises executing, on at least one processor of at least one computer, the following exemplary steps which are executed by the at least one processor.

In a (for example first) exemplary step, image data is acquired which describes the medical image being an image of a surface of a patient (for example, the skin) and a surface of at least one object (for example, a fixation device, such as an open face mask, and/or a medical instrument, such as a scalpel and/or an implant). The term object used herein is meant to refer to any object which is not part of the patient and which is for example a non-living object, for example a non-mammal object, for example a solid state body. In the medical image, the object may be in the foreground or the background relative to the patient. The object may be a patient support unit, a wall, a floor, or a ceiling.

The image data may be acquired by means of a 3D scanning device, such as a structured light scanning device, a time-of-flight scanning device, a light detection and ranging (LIDAR) device, analytical devices generating 3D data, like a CT scanner, a MR scanner, or a stereoscopic camera comprising two cameras having a parallax. The 3D scanning device is for example constituted to detect positions of elements of a surface of the patient or of the object.

In a (for example second) exemplary step, thermal data is acquired which describes a measured temperature of the surface of the patient and the surface of the at least one object. In one embodiment, the thermal data may be thermal image data. The thermal image data may describe a thermal image of the surface of the patient and the surface of the at least one object. The thermal data may be acquired by means of a thermal camera, for example infrared camera. The thermal data for example describing temperature values respectively associated with elements on a surface of the object or patient, the temperature values of the elements being detected by the thermal camera and for example represented in the thermal image as image elements having colour values.

In a (for example third) exemplary step, registration data is acquired which describes a relative spatial relationship between the acquiring of the image data and the acquiring of the thermal data. For example, the registration data are constituted to allow for image registration between the thermal data and the image data, for example transformation of thermal data and the image data into one common spatial coordinate system. In one embodiment, the registration data describes a relative position (i.e. location and orientation) of the 3D scanning device and the thermal camera. The registration data may also describe further (for example, optical) properties of the for acquiring the image data (e.g. 3D scanner) and/or the device for acquiring the thermal data (e.g. thermal camera), such as lens distortion parameters, orientation of the optical axis, focal distance and magnification.

In a (for example fourth) exemplary step, condition data is acquired which describes a condition for the measured temperature. The condition may relate to a temperature threshold. In one embodiment, the condition defines a temperature range below or above a predefined temperature (i.e. a temperature threshold). The predefined temperature may be related to the normal temperature of the skin of the patient. In one embodiment, the predefined temperature is in the range of 28° C. to 40° C., in particular 30° C. to 37° C., for example 28° C. to 33° C.

In one embodiment, the condition defines that the measured temperature has to be within a temperature range above a first predefined temperature and below a second predefined temperature (i.e. a temperature threshold). The first and/or second predefined temperature may be related to the normal temperature of the skin of the patient. In one embodiment, the first predefined temperature is in the range of 20° C. to 40° C., for example 25° C. to 35° C. and the second predefined temperature is in the range of 30° C. to 50° C., for example 40° C. to 45° C. The first predefined temperature and the second predefined temperature fulfil the condition that the first predefined temperature is lower than the second predefined temperature. In another embodiment, the condition defines only a lower limit for the measured temperature, i.e. that the measured temperature has to be above the above described first predefined temperature. In a further embodiment, the condition defines (only) an upper limit for the measured temperature, i.e. that the measured temperature has to be below the above described first predefined temperature. That latter case, for example relates to the identification of a surface of an object and for example defining this to be the region of interest. Using the second predefined temperature has in particular the advantage of reducing the risk of false measurements caused may be by external hot spots (e.g. light bulb).

In a (for example fifth) exemplary step, association data is determined based on the image data, the thermal data and the registration data, wherein the association data describes an association between at least one element of the image data and at least one element of the thermal data. For example, the association data describes an association between respective ones of elements of the image data and respective ones of elements of the thermal data. The element of the image data may be a pixel or voxel. The element of the image data may be described by a position vector, for example an XYZ vector. The position of the XYZ vector may be defined for any reference system, for example a reference system in which the thermal camera and/or the 3D scanner is at rest or a virtual reference system in which the image data and the thermal data are described. That is the image data describe positions of surface elements of the patient or the surface of the at least one object. The respective elements of the thermal data may be respective temperature values. Accordingly, the respective XYZ vector describing the respective element of the image data may be associated with a respective temperature value describing the respective element of the thermal data. In one embodiment, the association results in a quadruple (X,Y,Z,T), where X, Y, and Z describes the position of the surface element and T describes the temperature of the surface element. That is the association data can comprise a set, for example a plurality of quadruples. In one embodiment, the association data describes an association of all elements of the image data with elements of the thermal data. The association data may assign to each element of the image data (pixel or voxel) a temperature value. Accordingly, the association data may describe a fusion of the image data and the thermal data.

In a (for example sixth) exemplary step, condition compliance data is determined based on the condition data and the association data, wherein the condition compliance data describes a subset of the association data, wherein the subset fulfils the condition and includes a description of a part of the medical image. In one embodiment, the subset fulfils the condition that each element of the image data is associated to a temperature value below the predefined temperature (for example, the first predefined temperature). Accordingly, the subset may be associated with the surface of the object. In one embodiment, the subset fulfils the condition that each element of the image data is associated to a temperature value above the predefined temperature (for example, the first predefined temperature). Accordingly, the subset may be associated with the surface of the patient. By means of the condition compliance data the medical image may be partitioned in at least one region associated with the surface of the patient and at least one region associated with the surface of the at least one object.

By the above method a medical image may be partitioned automatically with a high accuracy. The part of the medical image described by the subset or a subregion of the part of the medical image may be tracked, for example during radiation treatment of a patient. The subregion may be for example determined by selecting it as described below.

In one embodiment, the part of the medical image described by the subset of the association data is associated with (for example, corresponds to) at least one cut-out region of an open face mask, for example for radiotherapy treatment. A plurality of cut-out regions may be associated with the part of the medical image described by the subset of the association data. A cut-out region of the plurality of cut-out regions is an example for the above mentioned subregion. According to another example, a part of the cut-out region is an example of the above mentioned subregion.

In one example, the part of the medical image or a subregion of the part of the medical image is a region of interest. The region of interest may correspond to an anatomical region of interest. Alternatively, the region of interest may correspond the object or part of the object. The part of the medical image or the subregion of the part of the medical image may be the region of interest for which a positional shift is determined by the method according to the second aspect described below.

For example, the cut-out region or part of the cut-out region of the open face mask may correspond to the above described subregion and may be defined as a region of interest. If a plurality of cut-out regions are associated with the part of the medical image described by the subset of the association data, one cut-out region may be selected manually or automatically as region of interest for further processing.

Selecting one subregion (which may be a cut-out region or a part thereof) may be performed based on the position, size, and/or shape of the cut-out region. For example, a subregion region associated with the forehead, eyes and/or nose of the patient may be selected. In particular, a subregion region upwards the upper lip of the patient may be selected. Selecting such a subregion region as the region of interest may be beneficial for tracking the region of interest during a radiation treatment, as explained below.

This selection may be performed based on user input or may be performed automatically based on different sizes or shapes of the subregions and/or based on temperature profile within the subregion and/or based on pattern recognition applied to the image part within the subregion (e.g. eye and/or nose detection).

The part of the medical image described by the subset of the association data or the subregion of the part of the medical image (which may be defined as a region of interest) may be a region which is integrally closed and apart from other regions of the medical image. Whether a region is integrally closed and apart from other regions is for example determined based on the temperature data. The boundary of the integrally closed region may be determined by means of a threshold for the temperature value associated to the respective image elements. For instance, image elements are defined to be a part of the integrally closed region if the temperature of the element is above the temperature and if the elements have a neighbouring element fulfilling the same condition. Alternatively or additionally, the boundary of the integrally closed region may be determined by means of a temperature gradient, for example by comparing the temperature values associated to neighbouring image elements. If the temperature gradient is above a predefined value, then the corresponding image are defined to belong to a boundary. The subregion may be a selected integrally closed region in the medical image (for example, a region being associated with a part within a cut-out region of an open face mask, see for example below: part above the upper lip).

In a second aspect, the invention is directed to computer-implemented medical method for determining a positional shift of a region of interest comprising the steps of the medical method according to the first aspect, wherein the part of the medical image or a subregion of the part of the medical image is the region of interest, wherein the method further comprises the following steps:
live image data is acquired which describes at least one subsequent medical image of the surface of the patient and the surface of the at least one object;
positional shift data is determined based on the live image data and the region of interest, wherein the positional shift data describes a positional shift of the region of interest.

There can be a plurality of subsequent medical images defining a sequence of images. The region of interest may undergo a positional shift within this sequence. The positional shift is for example relative to the boundary of the subsequent medical images. The positional shift of the region of interest may be determined by determining the change of position between the position of the region of interest in the medical image (i.e. the first image) and the position of the region of interest in any one of the subsequent medical images described by the live image data. In one embodiment the positional shift of the region of interest may be determined by determining the change of position between the position of the region of interest in one of the subsequent medical images described by the live image data and the position of the region of interest in another one of the subsequent medical images described by the live image data.

The positional shift data may be determined by means of a matching algorithm (for example, using similarity measures or elastic or rigid fusion, see below in the section "Definitions"), for example, an iterative closest point (ICP) algorithm. The general principle of an ICP algorithm is based on the assumption that if the correspondence of each point in a point cloud A to each point in a point cloud B is known, the registration result can be calculated by a simple function. Therefore, the ICP algorithm alternates iteratively over two steps: 1) correspondence analysis (guessing which point in point cloud A corresponds to which point in point cloud B), for example by means of a nearest neighbour search, and 2) calculate the result based on the correspondence analysis and shift point cloud A according to the result. The above described algorithms can be used for determining the region of interest in the subsequent medical images and thus the positional shift thereof. For example, a region may be determined which defines an image which has highest similarity to the image defined by the region of interest. The highest similarity may be for example defined by the highest similarity with respect to a depth profile described by the position vectors (e.g. XYZ vectors). For instance, a depth of the profile may be described by the Z coordinate and may be coded as a grey value and image matching algorithms may be used for determining the region matching with the region of interest.

For example, the positional shift data may be used for tracking the region of interest. For example, tracking may be performed by (for example, iteratively) determining positional shift data. The tracking may be performed during a radiation treatment. For example, a RGB-D tracking algorithm may be used for tracking. An RGB-D algorithm is a class of algorithms which uses colour and depth information for registration. The above mentioned ICP algorithm is a variation of an RGB-D tracking algorithm. For example, an ICP algorithm may be applied which receives xyzc (c for colour) as input points instead of xyz points.

In one embodiment, the method further comprises the following steps:
live thermal data is acquired which describes a current measured temperature of the surface of the patient and the surface of the at least one object;
wherein the positional shift data is further based on the live thermal data. The live image data describing the at least one subsequent medical image may be associated to live thermal data as described above with respect to the determination of the association data described with regard to the method according to the first aspect. For example, only those elements of the subsequent medical images are deemed to belong to the region of interest which fulfill the condition described by the condition data. This further insures the algorithm to be robust.

The positional shift data may be used for tracking the region of interest during a radiation treatment. The open face mask may help the patient to lie as still as possible during the treatment procedure. At the same time the cut-out region should be as big as possible leaving as much of the patient's surface as possible visible to, for example, the 3D scanner. This furthers a robust tracking.

When using an open face mask it is advantageous to track only the patient's surface and not the mask which is rigid by nature. However, tracking the face in open face mask in the typical radiation therapy setup is especially difficult due to flat angle perspective on the patient's surface, where self-occlusion often corrupts the surface. The above described method allows to accurately determine a positional shift of the region of interest and therefore to accurately track the region of interest.

Selecting a part in a cut-out region (as a subregion) upwards the upper lip of the patient as a region of interest to be tracked is advantageous during radiation treatment of a cranial tumour, because this region moves rigidly with the tumour when the patient is moving.

In a third aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect or according to the second aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect or according to the second aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention third to the second aspect therefore may alternatively or additionally relate to a data stream representative of the aforementioned program.

In a fourth aspect, the invention is directed to a non-transitory computer-readable program storage medium on which the program according to the second aspect is stored.

In a fifth aspect, the invention is directed to at least one computer (for example, a computer), comprising at least one processor (for example, a processor) and at least one memory (for example, a memory), wherein the program according to the third aspect is running on the processor or is loaded into the memory, or wherein the at least one computer comprises the computer-readable program storage medium according to the fourth aspect.

In a sixth aspect, the invention is directed to a medical system, comprising:
a) the at least one computer according to the fifth aspect;
b) a 3D scanning device;
c) a thermal camera,
   wherein the at least one computer is operably coupled to the 3D scanning device and the thermal camera for receiving the image data and the thermal data, respectively.

In a seventh aspect, the invention is directed to a radiation treatment system comprising:

the medical system according to the sixth aspect wherein the at least one computer performs the method according to the second aspect; and
a radiation treatment apparatus comprising a treatment beam source constituted to issue a treatment beam and a patient support unit (such as at least one of a patient bed or a headrest),
wherein the at least one computer is operably coupled to the radiation treatment apparatus for issuing a control signal to the radiation treatment apparatus for controlling, on the basis of the positional shift data, at least one of
the position of the treatment beam or
the position of the patient support unit.

More details about treatment beams are disclosed in the Section "Definitions" below.

For example, the invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity. The invention is instead directed as applicable to partition a medical image. For this reason alone, no surgical or therapeutic activity and in particular no surgical or therapeutic step is necessitated or implied by carrying out the invention.

The present invention also relates to a use of the system according to the seventh aspect for radiation treatment, wherein the use comprises execution of the steps of the method according the second aspect for determining the positional shift of the region of interest.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner.

The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy.

In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
a computer for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

The movements of the treatment body parts are for example due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analysing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part. Tracking an indicator body part thus allows a movement of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (for example, a fixed relative position relative to) the position of indicator structures (such as the thoracic wall, for example true ribs or false ribs, or the diaphragm or intestinal walls, etc.) which for example change their position due to vital movements.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
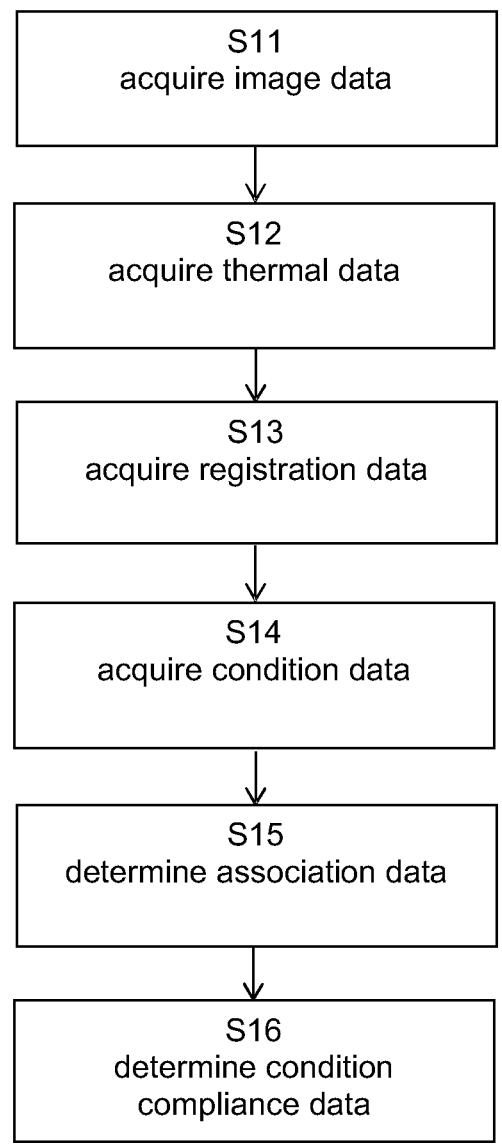
FIG. 1 is a flow diagram illustrating the basic steps of the method for partitioning a medical image according to the first aspect.

FIG. 1 illustrates the basic steps of the method for partitioning a medical image according to the first aspect, in which step S11 encompasses acquisition of the image data, step S12 encompasses acquisition of the thermal data, step S13 encompasses acquisition of the registration data, and step S14 encompasses acquisition of the condition data. The subsequent step S15 encompasses determining the association data. The last step S16 involves determination of the condition compliance data.

Figure 2:
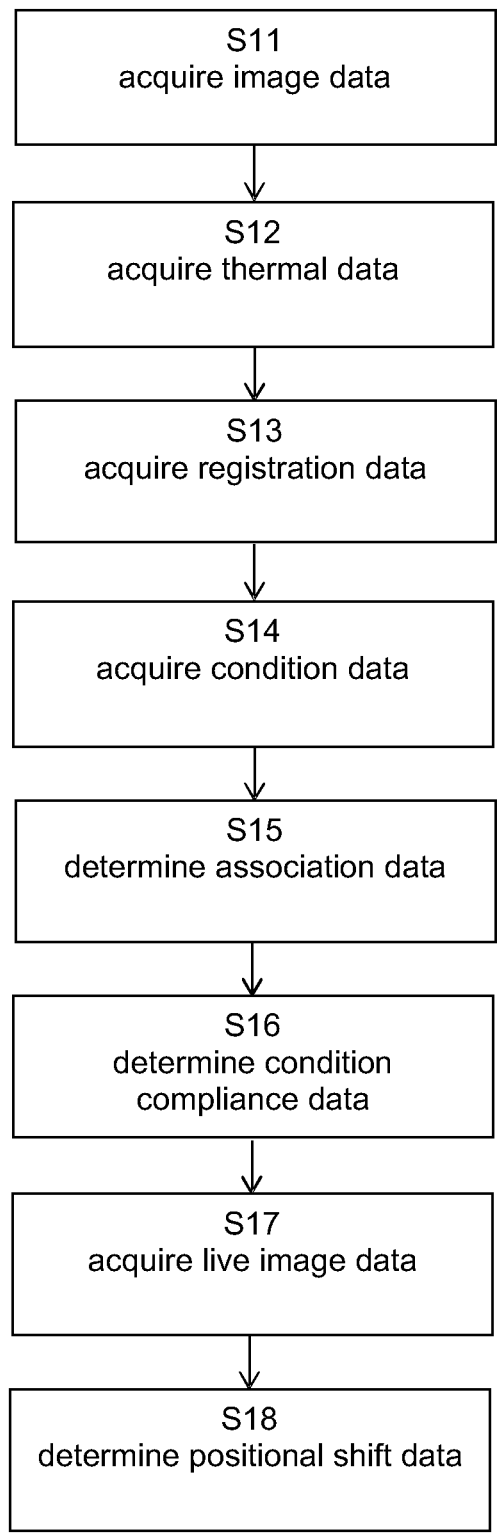
FIG. 2 is a flow diagram illustrating the basic steps of the method according to the first aspect.

FIG. 2 illustrates the basic steps of the method for determining a positional shift of the region of interest according to the second aspect. The method for determining a positional shift of the region of interest according to the second aspect comprises the steps S11 to S16 of the method for partitioning a medical image according to the first aspect. Furthermore, the method for determining a positional shift of the region of interest according to the second aspect comprises step S17 encompassing acquisition of live image data and step S18 encompassing determination of the positional shift data.

Figure 3:
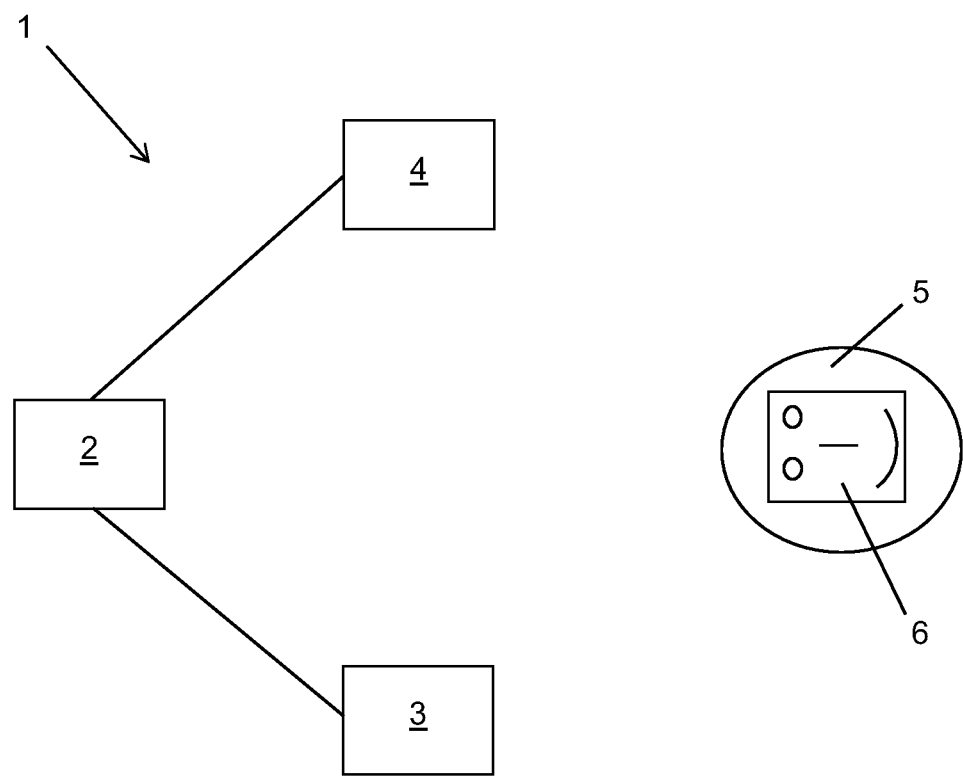
FIG. 3 is a schematic illustration of the medical system according to the sixth aspect.

FIG. 3 is a schematic illustration of the medical system 1 according to the sixth aspect. The medical system is in its entirety identified by reference sign 1 and comprises a computer 2, a 3D scanning device 3 and a thermal camera 4. The computer 2 is connected to the 3D scanning device 3 and the thermal camera 4 for receiving the thermal data and the image data, respectively. The connection may be wired or wireless. The components of the medical system 1 have the functionalities and properties explained above with regard to the sixth aspect of this disclosure.

Acquisition of the image data according to step S11 may be performed by means of the 3D scanning device 3. The acquired image data are transmitted to the computer 2. Acquisition of the thermal data according to step S12 may be performed by means of the thermal camera 4, for example by detecting an infrared image. The acquired thermal data are transmitted to the computer 2. FIG. 3 exemplarily shows an open face mask 5 fixed upon the head of a patient (reference sign 13 in FIG. 4). The open face mask 5 includes a cut-out region 6 exposing the face of the patient 13. The open face mask 5 is an example representing the at least one object in the image described by the image data. The cut-out region 6 corresponds to an example representing the part of the medical image described by the condition compliance data.

Figure 4:
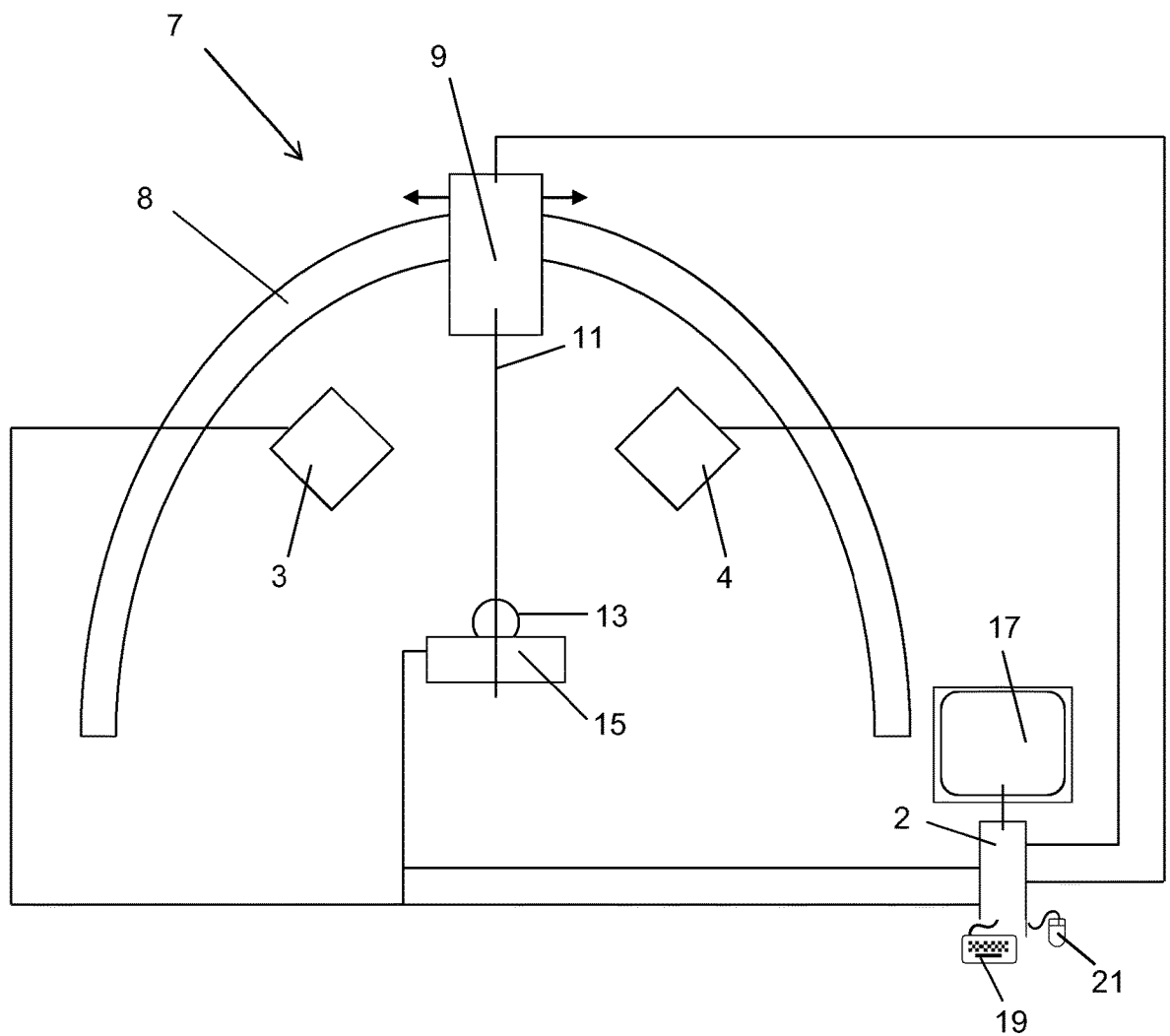
FIG. 4 is a schematic illustration of the radiation treatment system according to the seventh aspect.

FIG. 4 is s a schematic illustration of the radiation treatment system 7 according to the seventh aspect. The radiation treatment system is in its entirety identified by reference sign 7 and comprises the computer 2, the 3D scanning device 3 and the thermal camera 4. As shown by FIG. 4, the computer 2 may be connected to a monitor 17, a keyboard 19 and a mouse 21. Furthermore, the radiation treatment system 7 comprises a radiation treatment apparatus 9 comprising a treatment beam source constituted to issue a treatment beam 11 and a patient support unit 15 for carrying a patient 13. For example, the computer 2 is connected to the treatment apparatus 9 which can, for example, be moved along an arc 8. The computer can control the treatment apparatus 9, for example the position of the treatment beam by means of control signals. Alternatively or additionally, the computer 2 can be connected to the patient support unit 15 for changing the position of the patient support unit 15, for example by means of control signals. The position of the treatment beam 11 or the position of the patient support unit 15 is controlled on the basis of the positional shift data determined in step S18.

Figure 5:
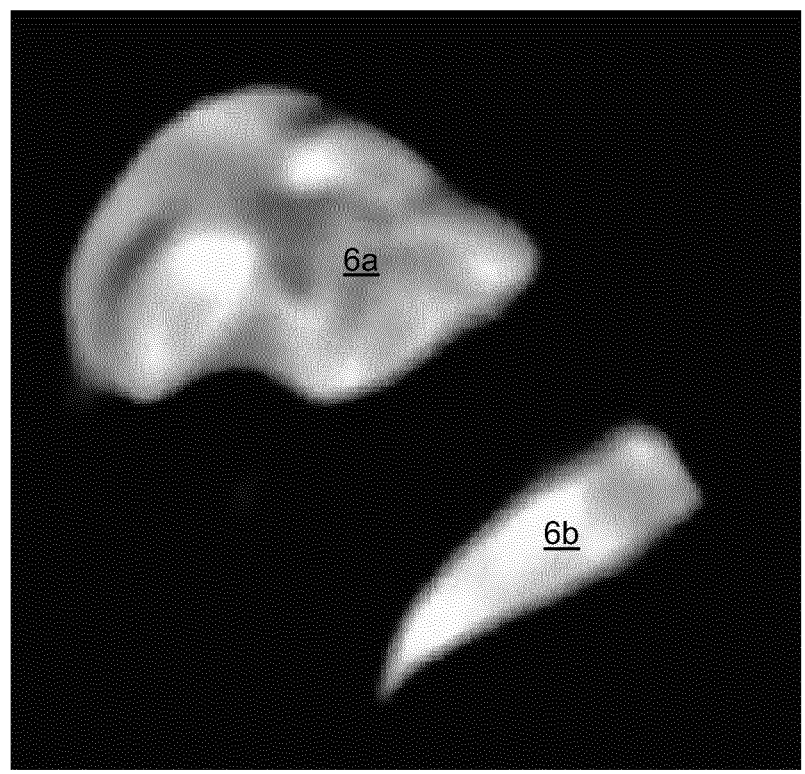
FIG. 5 shows an exemplary medical image partitioned by the method according to the first aspect.

FIG. 5 shows an exemplary medical image partitioned by the method according to the first aspect. Regions 6a and 6b correspond to the part of the medical image described by the condition compliance data determined in step S16. Regions 6a and Regions 6b may each represent a cut-out region, for instance in case the face mask includes two cut-out regions, one for the upper part of the face (above the upper lip), and one for the lower part of the face (below the upper lip). Alternatively, the regions 6a and 6b may represent subregions within one cut-out regions. Region 6a includes an area above the upper lip of the patient which moves rigidly with a cranial tumor to be treated by radiation therapy. Regions 6a may be selected manually or automatically as reference to be tracked during radiation treatment, i.e. may be selected as a region of interest. The regions 6a and 6b may be spaced apart due to the shape of the face mask or may be spaced apart due to the temperature distribution within the cut-out region. A selection of the region 6a as the region of interest may be automatically performed based on the size, position or shape of region 6a and/or 6b. For instance, the region 6a is larger than the region 6b.

The invention claimed is:

1. A computer-implemented method for partitioning a medical image, comprising:
acquiring image data which describes the medical image being an image of a surface of a patient and a surface of at least one object, wherein the image data is acquired from a 3D scanning device, wherein the 3D scanning device is one of a structured light scanning device, a time of flight scanning device, a light detection and ranging device or a stereoscopic camera having two cameras having a parallax;
acquiring thermal data which describes a measured temperature of the surface of the patient and the surface of the at least one object;
acquiring registration data which describes a relative spatial relationship between the acquiring of the image data and the acquiring of the thermal data;
acquiring condition data which describes a condition for the measured temperature;
determining association data based on the image data, the thermal data and the registration data, wherein the association data describes an association between at least one element of the image data and at least one element of the thermal data, wherein the association comprises associating a position vector describing the at least one element of the image data with a temperature value describing the at least one element of the thermal data;
determining condition compliance data based on the condition data and the association data, wherein the condition compliance data describes a subset of the association data, wherein the subset fulfils the condition and describes a part of the medical image.

2. The method according to claim 1, wherein the image data is acquired by means of a 3D scanning device and the thermal data is acquired by means of a thermal camera.

3. The method according to claim 2, wherein the registration data describes a relative position of the 3D scanning device and the thermal camera.

4. The method according to claim 1, wherein the part of the medical image is associated with at least one cut-out region of an open face mask.

5. The method according to claim 1, wherein the condition defines a temperature range below or above a predefined temperature.

6. The method according to claim 5, wherein the predefined temperature is within a range of about 28° C. to 40° C.

7. The method according to claim 1, wherein the part of the medical image or a sub region of the part of the medical image is a region of interest.

8. The method of claim 1 further comprising:
acquiring live image data which describes at least one subsequent medical image of the surface of the patient and the surface of the at least one object;
determining positional shift data based on the live image data and a region of interest, wherein the positional shift data describes a positional shift of the region of interest.

9. The method of claim 8, further comprising:
acquiring live thermal data which describes a current measured temperature of the surface of the patient and the surface of the at least one object;
wherein the positional shift data is further based on the live thermal data.

10. At least one non-transitory computer readable storage medium comprising instructions that, in response to execution of the instructions by one or more processors, cause the one or more processors to perform the following operations:
acquire image data which describes the medical image being an image of a surface of a patient and a surface of at least one object, wherein the image data is acquired from a 3D scanning device, wherein the 3D scanning device is one of a structured light scanning device, a time of flight scanning device, a light detection and ranging device or a stereoscopic camera having two cameras having a parallax;
acquire thermal data which describes a measured temperature of the surface of the patient and the surface of the at least one object;
acquire registration data which describes a relative spatial relationship between the acquiring of the image data and the acquiring of the thermal data;
acquire condition data which describes a condition for the measured temperature;
determine association data based on the image data, the thermal data and the registration data, wherein the association data describes an association between at least one element of the image data and at least one element of the thermal data wherein the association comprises associating a position vector describing the at least one element of the image data with a temperature value describing the at least one element of the thermal data;
determine condition compliance data based on the condition data and the association data, wherein the condition compliance data describes a subset of the association data, wherein the subset fulfils the condition and describes a part of the medical image.

11. A medical system for partitioning a medical image, comprising:
at least one computer having at least one processor and associated memory;
a 3D scanning device;
a thermal camera;
the associated memory on the at least one computer having instructions, which when executed by the at least one processor causes the at least one computer to:
acquire image data which describes the medical image being an image of a surface of a patient and a surface of at least one object, wherein the image data is acquired from a 3D scanning device, wherein the 3D scanning device is one of a structured light scanning device, a time of flight scanning device, a light detection and ranging device or a stereoscopic camera having two cameras having a parallax;
acquire thermal data which describes a measured temperature of the surface of the patient and the surface of the at least one object;
acquire registration data which describes a relative spatial relationship between the acquiring of the image data and the acquiring of the thermal data;
acquire condition data which describes a condition for the measured temperature;
determine association data based on the image data, the thermal data and the registration data, wherein the association data describes an association between at least one element of the image data and at least one element of the thermal data wherein the association comprises associating a position vector describing the at least one element of the image data with a temperature value describing the at least one element of the thermal data;

determine condition compliance data based on the condition data and the association data, wherein the condition compliance data describes a subset of the association data, wherein the subset fulfils the condition and describes a part of the medical image;

wherein the at least one computer is operably coupled to the 3D scanning device and the thermal camera for receiving the image data and the thermal data.

12. A radiation treatment system comprising:

at least one computer having at least one processor and associated memory;

a 3D scanning device;

a thermal camera;

the associated memory on the at least one computer having instructions, which when executed by the at least one processor causes the at least one computer to:

acquire image data which describes the medical image being an image of a surface of a patient and a surface of at least one object, wherein the image data is acquired from a 3D scanning device, wherein the 3D scanning device is one of a structured light scanning device, a time of flight scanning device, a light detection and ranging device or a stereoscopic camera having two cameras having a parallax;

acquire thermal data which describes a measured temperature of the surface of the patient and the surface of the at least one object;

acquire registration data which describes a relative spatial relationship between the acquiring of the image data and the acquiring of the thermal data;

acquire condition data which describes a condition for the measured temperature;

determine association data based on the image data, the thermal data and the registration data, wherein the association data describes an association between at least one element of the image data and at least one element of the thermal data, wherein the association comprises associating a position vector describing the at least one element of the image data with a temperature value describing the at least one element of the thermal data;

determine condition compliance data based on the condition data and the association data, wherein the condition compliance data describes a subset of the association data, wherein the subset fulfils the condition and describes a part of the medical image;

wherein the at least one computer is operably coupled to the 3D scanning device and the thermal camera for receiving the image data and the thermal data;

acquire live image data which describes at least one subsequent medical image of the surface of the patient and the surface of the at least one object;

determine positional shift data based on the live image data and a region of interest, wherein the positional shift data describes a positional shift of the region of interest;

a radiation treatment apparatus having a treatment beam source operable to issue a treatment beam and a patient support unit, wherein the at least one computer is operably coupled to the radiation treatment apparatus for issuing at least a control signal to the radiation treatment apparatus for controlling, on the basis of the positional shift data, at least one of:

the position of the treatment beam, or the position of the patient support unit.

* * * * *